United States Patent [19]

Suami et al.

[11] 4,387,220
[45] Jun. 7, 1983

[54] NITROSOUREA DERIVATIVES OF SUCROSE

[75] Inventors: Tetsuo Suami, 3-5-8, Nakamachi, Musashino-shi, Tokyo, Japan; Yushi Itoh, Higashikurume; Shuichi Oki, Tokyo, both of Japan

[73] Assignees: The Nissin Sugar Manufacturing Co., Ltd.; Tetsuo Suami, both of Tokyo, Japan

[21] Appl. No.: 313,360

[22] Filed: Oct. 20, 1981

[30] Foreign Application Priority Data

Nov. 5, 1980 [JP] Japan .................................. 55-155443
Jun. 23, 1981 [JP] Japan .................................. 56-96863

[51] Int. Cl.$^3$ ....................... C08B 37/00; A61K 31/70
[52] U.S. Cl. ........................................ 536/53; 424/180
[58] Field of Search .......................................... 536/53

[56] References Cited

U.S. PATENT DOCUMENTS 4,180,655 12/1979 Suami .................................... 536/53
4,251,515 2/1981 Suami .................................... 536/53

FOREIGN PATENT DOCUMENTS 3788 2/1979 European Pat. Off. .............. 536/53

OTHER PUBLICATIONS

Roberts "Basic Principles of Org. Chem." (1964) p. 531.
Carey "Advanced Org. Chem." 1978, pp. 340, 341.

*Primary Examiner*—A. Siegel

*Attorney, Agent, or Firm*—Frishhauf, Holtz, Goodman & Woodward

[57] ABSTRACT

Novel nitrosourea derivatives of sucrose having a structure expressed by the general formula:

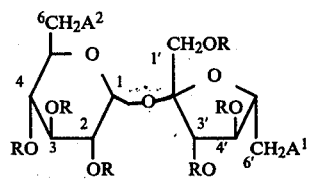

wherein $A^1$ and $A^2$ denote a group of OR or

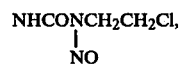

either $A^1$ or $A^2$ represents a group of

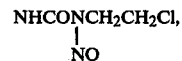

and R shows a hydrogen atom or acyl group, and a method of manufacturing said derivatives. Said novel nitrosourea derivatives of sucrose have antitumor activity.

5 Claims, No Drawings

NITROSOUREA DERIVATIVES OF SUCROSE

BACKGROUND OF THE INVENTION (a) Field of the Invention

This invention relates to novel nitrosourea derivatives of sucrose expressed by the general structural formula:

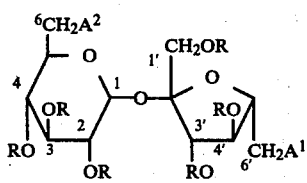
(I)

where $A^1$ and $A^2$ are a group of OR or $$\underset{\underset{NO}{|}}{NHCO}NCH_2CH_2Cl,$$

and either $A^1$ or $A^2$ is group of $$\underset{\underset{NO}{|}}{NHCO}NCH_2CH_2Cl,$$

and R is a hydrogen atom or acyl group.

A compound embodying this invention has a significant antitumor activity and yet an extremely small side effect giving rise to, for example, spleen atrophy, and consequently can be applied very effectively as a medicine.

(b) Description of the Prior Art

The Japanese patent publication No. 32,768 (1979) sets forth a compound having a structure expressed by the general formula:

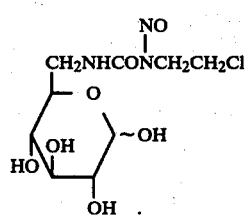

The Japanese patent disclosure (KOKAI) No. 151,918 (1979) discloses a nitrosourea derivative having a structure expressed by the general formula:

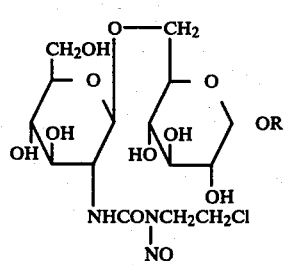

where R is a hydrogen atom, alkyl group, or aryl group.

The Japanese patent disclosure No. 19,944 (1979) indicates a compound having a structure expressed by the general formula:

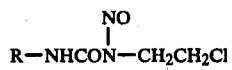

where R represents

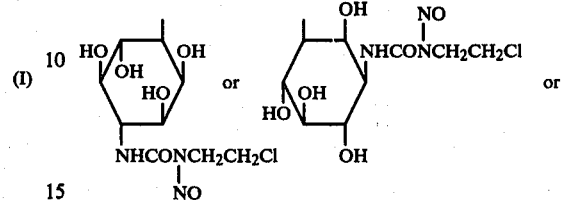
or
or

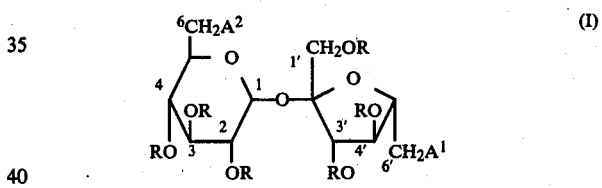

The above-listed disclosed compounds are all known to have an antitumor activity.

SUMMARY OF THE INVENTION

It is accordingly the object of this invention to provide novel nitrosourea derivatives of sucrose having a structure expressed by the general formula:

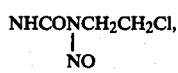
(I)

where $A^1$ and $A^2$ denote a group of OR or $$\underset{\underset{NO}{|}}{NHCO}NCH_2CH_2Cl,$$

and either $A^1$ or $A^2$ represents said $$\underset{\underset{NO}{|}}{NHCO}NCH_2CH_2Cl$$

group, and R is a hydrogen atom or acyl group.

DETAILED DESCRIPTION OF PREFERRED EMBODIMENTS

A compound embodying this invention can be prepared as the nitroso form from ureido derivatives of sucrose having a structure expressed by the general formula:

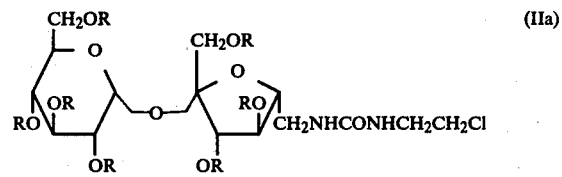
(IIa)

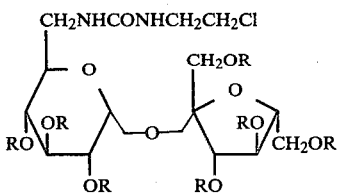

where R denotes the same thing as in the above-mentioned general formula (I). A nitrosation reagent used in the invention includes, for example, the known alkali metal nitrite, nitrogen trioxide, nitrogen tetraoxide and nitrosyl chloride. Preferred alkali metal nitrites include sodium nitrite and potassium nitrite. A reaction solvent includes, for example, organic solvents such as acetone, methanol, ethyl acetate, ether, dioxane and tetrahydrofuran, organic acids such as formic acid, and acetic acid and aqueous solutions thereof and aqueous solutions of mineral acids such as sulfuric acid. With the present invention, reaction is generally carried out at a temperature ranging between −10° C. and 30° C. After reaction, the product is purified, if necessary, by an ion exchange resin or silica gel.

A product embodying this invention can be prepared from amino derivatives of sucrose having a structure expressed by the general formula (IIIa) or (IIIb):

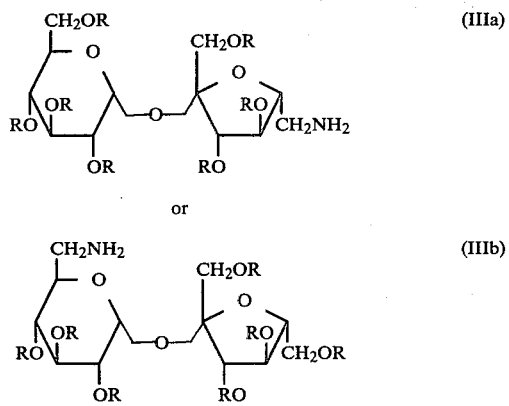

(where R denotes the same thing as in the preceding general formulas) or the acid salts of said amino derivatives with N-(2-chloroethyl)-N-nitrosocalbamate phenyl derivatives having a structure expressed by the general formula:

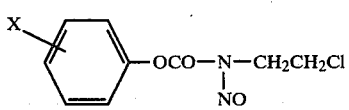

The reaction is generally carried out at a temperature ranging from −20° C. to 60° C. A reaction solvent includes organic solvents such as methanol, ethanol, acetone, ethyl acetate, ether, dioxane and tetrohydrofuran. After reaction, the intended product whose structure is expressed by the general formula (I) is obtained by applying the known purification process such as the removal of a solvent, crystallization, or column chromatography. The compound of the invention whose structure is expressed by the general formula (I) in which at least one R denotes an acyl group and the other "R"s represent a hydrogen atom can also be prepared by acylating a compound whose structure is expressed by the general formula (I) in which all the "R"s denote a hydrogen atom by the employment of, for example, aliphatic acid anhydride, aliphatic acid halide or aliphatic acid ester.

Description is now given in the results of experiments made with animals to prove the antileukemic activity of a compound prepared by the method of this invention.

Animal tests

Animals tested: Each group consisting of four or five male $CDF_1$ mice (each 6 weeks old and weighing $24 \pm 2$ g)

Compounds tested

Compound 1:
6'-[[[(2-chloroethyl)nitrosoamino]carbonyl]amino]-6'-deoxysucrose

Compound 2:
6'-[[[(2-chloroethyl)nitrosoamino]carbonyl]amino]-6'-deoxysucrose heptaacetate Compound 3:
6-[[[(2-chloroethyl)nitrosoamino]carbonyl]amino]-6-deoxysucrose Compound 4:
6-[[[(2-chloroethyl)nitrosoamino]carbonyl]amino]-6-deoxysucrose heptaaccetate Method of the experiment $1 \times 10^5$ of lymphoid.Leukemia L1210 cells were transplanted into the abdominal cavity of mice. After 24 hours, the compounds 1 to 4 were respectively administered to the above-mentioned each group consisting of five male mice. Observation was continued for 60 days.

Results of the experiment

The following table indicates the average survival days of the tested mice, their ILS (increase in life span) and the number of mice which survived for over 60 days.

TABLE 1

| Compound tested | Dose (mg/kg) | Average survival day (number of days*[1]) | ILS*[2] (%) | Number of mice survived for over 60 days |
|---|---|---|---|---|
| Compound 1 | 100 | >60 | >757 | 3/4 |
| | 50 | 21 | 200 | 1/4 |
| | 30 | 14 | 100 | 1/4 |
| | 20 | 12 | 71 | 0/4 |
| Compound 2 | 100 | 13 | 86 | 0/4 |
| | 50 | 12 | 71 | 0/4 |
| | 30 | 11.5 | 64 | 0/4 |
| | 20 | 10 | 43 | 0/4 |
| Compound 3 | 150 | >60 | >650 | 4/5 |
| | 100 | >60 | >650 | 4/5 |
| | 50 | 18 | 125 | 2/5 |
| | 20 | 11 | 38 | 0/5 |
| | 10 | 11 | 38 | 0/5 |
| Compound 4 | 50 | 12 | 50 | 0/5 |
| | 20 | 12 | 50 | 0/5 |
| | 10 | 11 | 38 | 0/5 |
| Control | | 7** | 0 | 0/4 |

TABLE 1-continued

| Compound tested | Dose (mg/kg) | Average survival day (number of days*[1]) | ILS*[2] (%) | Number of mice survived for over 60 days |
|---|---|---|---|---|
| (saline) | | 8*** | | |

*[1] The average survival day of the tested mice are expressed in MSD (median survival days).

*[2] ILS (increase in life span) (%) = $\frac{\text{(MSD treated)} - \text{(MSD control)}}{\text{(MSD control)}} \times 100$ (%)

**Result for the control for Compounds 1 and 2
***Result for the control for Compounds 3 and 4

The results of the above-mentioned experiments prove that the compounds of this invention has a high survival effect on the mice suffering from leukemia L1210, namely, displayed a prominent antileukemic activity. Where R of the general structural formula denoted the acyl group instead of the acetyl group, substantially the same effect was assured.

Description is now given in reference with the preparation method of an ureido derivative of sucrose which has a structure expressed by the general formula (IIa) and is used as the starting material of the compound embodying this invention.

Reference 1

Preparation of 6′-[[[(2-chloroethyl)amino]carbonyl]amino]-6′-deoxysucrose heptaacetate (in the case where all the "R"s in the general structural formula (IIa) represent an acethyl group)

A 500 mg portion of 6′-amino-6′-deoxysucrose prepared by Suami's process (refer to Bulletin of the Chemical Society of Japan, 48, 1953 (1975) was dissolved in 4 ml of water-containing methanol. 0.3 ml of 2-chloroethyl isocyanate was added with ice cooling and agitation. After 3 hours, the reaction solution was concentrated in vacuo. The residue was treated with 5 ml of acetic anhydride and 5 ml of pyridine. The mixture was allowed to stand overnight at room temperature, and then concentrated in vacuo. The residue was purified by silica gel column chromatography (soluvent: a mixed solution of henzene and acetone bearing the ratio of 5:1) to give 6′-[[[(2-chloroethyl)amino]carbonyl]amino]-6′-deoxysucrose haptaacetate as a colorless glass-like mass.

Yield: 756 mg (76%).
Melting point: 61° to 63° C.
$[\alpha]_D^{20}$: +66.0° (C 3.1, chloroform).
Infrared Spectrum: 1560, 1650 cm$^{-1}$ (ureido), 1750 (acetyl).

| Elemental analysis of $C_{29}H_{41}N_2O_{18}Cl$ (having a molecular weight of 741.11) | | |
|---|---|---|
| Calculated value: | C | 47.00 |
| (%) | H | 5.58 |
| | N | 3.78 |
| | Cl | 4.78 |
| Experimental value: | C | 47.24 |
| (%) | H | 5.57 |
| | N | 3.56 |
| | Cl | 4.86 |

Reference 2

Preparation of 6′-[[[(2-chloroethyl)amino]carbonyl]amino]-6′-deoxysucrose (in the case where all the "R"s in the general structural formula (IIa) denote a hydrogen atom)

A 200 mg portion of 6′-amino-6′-deoxysucrose was dissolved in 4 ml of water-containing methanol, 0.2 ml of 2-chloroethyl isocyanate was added under ice cooling and agitation. After 1 hour, the solution was washed with ethyl acetate. The aqueous layer was concentrated in vacuo. The resultant glass-like residue was treated with ethanol and ether to give 6′-[[[(2-chloroethyl)amino]carbonyl]amino]-6′-deoxysucrose as powder.

Yield: 181 mg (71%).
Melting point: 120° to 125° C.
$[\alpha]_D^{22}$: +78.3° (C 1.8, ethanol).
Infrared spectrum: 1570, 1640 cm$^{-1}$ (ureido).

| Elemental analysis of $C_{15}H_{27}N_2O_{11}Cl$ (having a molecular weight of 446.85) | | |
|---|---|---|
| Calculated value: | C | 40.32 |
| (%) | H | 6.09 |
| | N | 6.27 |
| | Cl | 7.93 |
| Experimental value: | C | 40.21 |
| (%) | H | 6.18 |
| | N | 5.98 |
| | Cl | 7.76 |

Description is now given in reference with the preparation method of a ureido derivative of sucrose which has a structure expressed by the general formula (IIb) and is used as the starting material of the compound embodying this invention.

Reference 3

Preparation of 6-[[[(2-chloroethyl)amino]carbonyl]amino]-6-deoxysucrose (in the case where all the "R"s in the general structural formula (IIb) denote a hydrogen atom)

A 300 mg portion of 6-amino-6-deoxysucrose was dissolved in 5 ml methanol containing 50% of water. 200 microliters of 2-chloroethyl isocyanate was dropped into said solution under ice cooling and agitation. After 1 hour, the solution was washed with ethyl acetate. The resultant aqueous layer was concentrated in vacuo to give a colorless glass-like residue. When treated with ethanol and ether, the residue was solidified to give 6-[[[(2-chloroethyl amino]carbonyl]amino]-6-deoxysucrose as powder.

Yield: 349 mg (89%).
$[\alpha]_D^{22}$: +25.2° (C 2.3, ethanol).
Melting point: 103° C.
Beilstein test: Positive (Cl).
Infrared spectrum: 1560 cm$^{-1}$ (ureido, NH), 1640 cm$^{-1}$ (ureido, C=O).

| Elemental analysis of $C_{15}H_{27}N_2O_{11}Cl$ (having a molecular weight of 446.85): | | |
|---|---|---|
| Calculated value: | C | 40.32 |
| (%) | H | 6.09 |
| | N | 6.27 |
| | Cl | 7.93 |
| Experimental value: | C | 40.00 |
| (%) | H | 6.12 |
| | N | 5.99 |

| Elemental analysis of $C_{15}H_{27}N_2O_{11}Cl$ (having a molecular weight of 446.85): | | |
|---|---|---|
| | Cl | 7.71 |

Reference 4

Preparation of 6-[[[(2-chloroethyl)amino]carbonyl]amino]-6-deoxysucrose hepta-acetate (in the case where all the "R"s in the general formula (IIb) denote an acetyl group)

A 200 mg portion of 6-[[[(2-chloroethyl)amino]carbonyl]amino]-6-deoxysucrose was treated with 1 ml of acetic anhydride and 1 ml of pyridine. The mixture was allowed to stand overnight at room temperature. The solution was concentrated in vacuo. The concentrated residue was purified by the silica gel column chromatography (solvent: a mixture of benzene and acetone bearing the ratio of 5:1) to give 6-[[[(2-chloroethyl)amino]carbonyl]amino]-6-deoxysucrose heptaacetate.

Yield: 239 mg (72%).
$[\alpha]_D^{21}$: +63.3° (C 1.5, chloroform).
Melting point: 57° C.
Beilstein test: Positive (Cl).
Infrared spectrum: 1560 cm$^{-1}$ (ureido, NH); 1650 cm$^{-1}$ (ureido, C=O); 1750 cm$^{-1}$ (acetyl, C=O).
$^1$H nuclear magnetic resonance spectrum (60 MHz, CDCl$_3$/TMS): δ2.00 (s, 3H, OAc), 2.07 (s, 6H, OAc×2), 2.14 (s, 12H, OAc×4), 4.80 (dd, 1H, $J_{2,3}$=3.61 Hz, $J_{2,3}$=9.42 Hz, H-2), 4.85 (t, 1H, $J_{2,3}$=$J_{3,4}$=9.42 Hz, H-3), 5.77 (d, 1H, $J_{1,3}$=3.61 Hz, H-1).

| Elemental analysis of $C_{29}H_{41}N_2O_{18}Cl$ (having a molecular weight of 741.11): | | |
|---|---|---|
| Calculated value: | C | 47.00 |
| (%) | H | 5.58 |
| | N | 3.78 |
| | Cl | 4.78 |
| Experimental value: | C | 47.10 |
| (%) | H | 5.50 |
| | N | 3.78 |
| | Cl | 4.72 |

Description now given in reference with the preparation method of an amino derivative of sucrose which has a structure expressed by the general formula (IIIb) and is used as the starting material of the compound embodying this invention.

Reference 5

Preparation of 6-amino-6-deoxysucrose having a structure expressed by the general formula (IIIb) (in the case where all the "R"s in the general formula denote a hydrogen atom)

(1) Preparation of 6-O-mesitylenesulfonylsucrose hepta-acetate 5.73 g of 1', 2, 3, 3', 4, 4', 6'-hepta-O-acetyl sucrose prepared by the process proposed by Otake (Bulletin of Chemical Society of Japan, 43, 3199 (1970)) was dissolved in 100 ml of dry pyridine. 5.7 g of mesitylenesulfonyl chloride was added to the solution. Reaction was carried out 42 hours at room temperature. The solution was poured into 1 l of ice cold water, and then chloroform extraction was carried out. The chloroform layer was washed with water, dried over anhydrous sodium sulfate, and concentrated in vacuo to give a glass-like residue. The residue was purified by silica gel column chromatography (soluvent: a mixture of methyl ethyl ketone and toluene bearing a ratio of 1:3). As a result, the intended 6-O-mesitylenesulfonylsucrose heptaacetate was obtained as glass.

Yield: 5.36 g (73%).
Melting point: 42° C.
$[\alpha]_D^{22}$: +60.6° (C 3.1, chloroform).

| Infrared spectrum: | 1180 cm$^{-1}$ (SO$_2$) |
|---|---|
| | 1600 cm$^{-1}$ 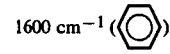 |
| | 1750 cm$^{-1}$ (acetyl, C=O) |

| $^1$H nuclear magnetic resonance spectrum (60 MHz, CDCl$_3$/TMS): |
|---|
| δ 2.01 (s, 6H, OAc × 2), 2.08 (s, 3H, OAc), |
| 2.11 (s, 9H, OAc × 3), 2.16 (S, 3H, OAc), |
| 2.32 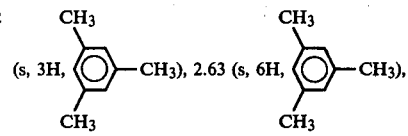 |
| 4.74 (dd, 1H, $J_{1,2}$ = 3.61Hz, $J_{2,3}$ = 9.22Hz, H-2), |
| 5.05 (t, 1H, $J_{2,3}$ = $J_{3,4}$ = 9.22Hz, H-3), |
| 5.64 (d, 1H, $J_{1,2}$ = 3.61Hz, H-1), |
| 7.03 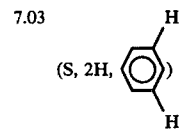 |

| Elemental analysis of $C_{35}H_{46}O_{20}S$ (having a molecular weight 818.82): | | |
|---|---|---|
| Calculated value: | C | 51.34 |
| (%) | H | 5.66 |
| | S | 3.92 |
| Experimental value: | C | 51.11 |
| (%) | H | 5.61 |
| | S | 4.18 |

(2) Preparation of 6-azido-6-deoxysucrose heptaacetate 4.97 g of 6-O-mesitylenesulfonylsucrose heptaacetate was dissolved in 100 ml of 90% aqueous 2-methoxyethanol. The solution was heated under reflux with 2.5 g of sodium azido for 17 hours. A residue obtained after concentration was treated with 25 ml of acetic anhydride, and 25 ml of dry pyridine. The mixture was allowed to stand overnight at room temperature. Insoluble matter were filtered off. The filtrate was concentrated in vacuo. The resultant syrup-like residue was purified by silica gel column chromatography (solvent: a mixture of benzene and acetone bearing a ratio of 9:1) to give 6-azido-6-deoxysucrose heptaacetate.

Yield: 3.28 g (82%).
$[\alpha]_D^{25}$: +76.1° (C 2.5, chloroform).
Infrared spectrum: 1750 cm$^{-1}$ (acetyl, C=O); 2100 cm$^{-1}$ (N$_3$).

$^1$H nuclear magnetic resonance spectrum (60 MHz, CDCl$_3$/TMS): δ2.01 (s, 3H, OAc), 2.03 (s, 3H, OAc), 2.07 (s, 3H, OAc), 2.09 (s, 9H, OAc×3), 2.16 (s, 3H, OAc), 3.40 (m, 2H, 6—CH$_2$), 4.82 (dd, 1H, J$_{1,2}$=3.41 Hz, J$_{2,3}$=9.42 Hz, H-2), 5.05 (t, 1H, J$_{1,2}$=3.41 Hz, H-1).

| Elemental analysis of C$_{26}$H$_{35}$N$_3$O$_{17}$ (having a molecular weight of 661.59): | | |
|---|---|---|
| Calculated value: | C | 47.20 |
| (%) | H | 5.33 |
|  | N | 6.35 |
| Experimental value: | C | 47.42 |
| (%) | H | 5.43 |
|  | N | 6.10 |

(3) Preparation of 6-amino-6-deoxysucrose

A 3.28 g portion of 6-azido-6-deoxysucrose heptaacetate was dissolved in 30 ml of 0.1 M sodium methoxide/methanol. The solution was allowed to stand overnight at room temperature. Sodium ion was removed from the solution with an ion exchange resin Amberlite IR-120B (H+). The solution thus treated was concentrated in vacuo to give a colorless acethyl-free product as a glass. The glassy mass was dissolved in 100 ml of 50% aqueous ethanol. Reduction was continued with stirring for 5 hours at 40° C. in the presence of 200 mg of platinum oxide with the initial hydrogen pressure set at 3.4 kg/cm$^2$. The catalyst was filtered off. The filtrate was concentrated in vacuo to give glass-like residue. This residue was solidified with ethanol to give 6-amino-6-deoxysucrose as amorphous powder.

Yield: 1.44 g (78%).

[α]$_D^{22}$: +53.2° (C 2.5, water).

Melting point: 65°.

Ninhydrin reaction: Positive (purple).

$^1$H nuclear magnetic resonance spectrum (60 MHz, D$_2$O/DSS): δ5.06 (d, 1H, J$_{1,2}$=3.21 Hz, H-1).

| Elemental analysis of C$_{12}$H$_{23}$NO$_{10}$.½H$_2$CO$_3$ (having a molecular weight of 349.06): | | |
|---|---|---|
| Calculated value: | C | 41.72 |
| (%) | H | 6.71 |
|  | N | 4.01 |
| Experimental value: | C | 41.75 |
| (%) | H | 6.64 |
|  | N | 3.62. |

This invention is further detailed with reference to the examples in which R given in the aforementioned general structural formula denotes a hydrogen atom and an acetyl group. Obviously, the product of this invention can be prepared substantially by the same process as applied in the examples, even where R represents another acyl group, for example, an acetyl group.

EXAMPLE 1

Preparation of 6'-[[[(2-chloroethyl)nitrosoamino]carbonyl]amino]-6-deoxysucrose (compound 1) (in the case where all the "R"s given in the general structural formula (I) denote a hydrogen atom, A$^1$ represents a group of

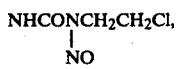

and A$^2$ indicates OR).

A 105 mg portion of 6'-amino-6'-deoxysucrose prepared by a process proposed by Suami (Bulletin of Chemical Society of Japan, 48, 1953 (1975) was dissolved in 2 ml of water, 37 mg of triethylamine was added to the solution. The resultant liquid was concentrated in vacuo to give a white crystalline residue. The residue was washed with several milliliters of ether. The washed mass was then suspended in 6 ml of methanol. A solution prepared by dissolving 230 mg of p-nitrophenyl-N-(2-chloroethyl)-N-nitrosocarbamate in 6 ml of tetrahydrofuran was dropped into the above-mentioned suspension at room temperature under stirring. After 12 hours, the reaction mixture was concentrated in vacuo, causing excess p-nitrohenyl-N-(2-chloroethyl)-N-nitrosocarbamate to crystallize out. The crystallized mass was filtered off. The fitrate was concentrated in vacuo to give a yellow oily residue. The residue was washed with isopropyl ether, and then fully dried to give 6'-[[[(2-chloroethyl)nitrosoamino]carbonyl]amino]-6'-deoxysucrose (compound 1) as an amorphous solid.

Yield: 130 mg (97%).

Melting point: 61° (accompanied with foaming).

[α]$_D^{23}$: +39.5° (C 0.38, water).

Infrared spectrum: 1495 cm$^{-1}$ (nitroso); 1530, 1725 cm$^{-1}$ (ureido).

| Elemental analysis of C$_{15}$H$_{26}$N$_3$O$_{12}$Cl (Having a molecular weight of 475.839): | | |
|---|---|---|
| Calculated value: | C | 37.86 |
| (%) | H | 5.51 |
|  | N | 8.83 |
|  | Cl | 7.45 |
| Experimental value: | C | 37.52 |
| (%) | H | 5.79 |
|  | N | 8.50 |
|  | Cl | 7.78. |

EXAMPLE 2

Preparation of 6'-[[[(2-chloroethyl)nitrosoamino]carbonyl]amino]-6'-deoxysucrose heptaacetate (compound 2) (in the case where all the "R"s given in the general structural formula (I) denote an acetyl group, A$^1$ indicates a group of

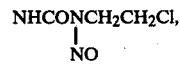

and A$^2$ represents a group of OR).

457 mg of 6'-[[[(2-chloroethyl)amino]carbonyl]amino]-6'-deoxysucrose heptaacetate was dissolved in 6 ml of formic acid. 64 mg of sodium nitrite was added to the solution under ice cooling and stirring. After 1 hour, the reaction mixture was poured into ice cold water. Extraction was carried out with chloroform. The chloroform layer was washed with water, dried over anhydrous sodium sulfate. The dried solution was concentrated in vacuo to give a pale yellow glass-like residue. The residue was purified by the silica gel column chromatography (solvent: a mixture of benzene and acetone bearing a ratio of 10:1) to give 6'-[[[(2-chloroethyl)nitrosoamino]carbonyl]amino]-6'-deoxysucrose heptaacetate (compound 2) as pale yellow glass.

Yield: 374 mg (79%).

Melting point: 50° to 52° C.

$[\alpha]_D^{20}$: +56.2° (C 1.7, chloroform).

Infrared spectrum: 1500 cm$^{-1}$ (nitroso); 1540 cm$^{-1}$ (NH); 1750 cm$^{-1}$ (acetyl).

$^1$H nuclear magnetic resonance spectrum (60 MHz, CDCl$_3$/TMS): δ 1.99 (s, 3H, Ac), 2.02 (s, 3H, Ac), 2.04 (s, 3H, Ac), 2.06 (s, 3H, Ac), 2.08 (S, 3H, Ac), 2.10 (s, 3H, Ac), 2.13 (s, 3H, Ac), 3.45 (t, 2H, J=5.97 Hz, NCH$_2$C$\underline{H}_2$Cl), 4.79 (dd, 1H, J$_{1,2}$=4.18 Hz, J$_{2,3}$=9.95 Hz, H-2), 7.42 (broad, 1H, N$\underline{H}$).

| Elemental analysis of C$_{29}$H$_{40}$N$_3$O$_{19}$Cl (having a molecular weight of 770.11): | | |
|---|---|---|
| Calculated value: | C | 45.23 |
| (%) | H | 5.24 |
|  | N | 5.46 |
|  | Cl | 4.60 |
| Experimental value: | C | 45.12 |
| (%) | H | 5.19 |
|  | N | 5.30 |
|  | Cl | 4.80 |

EXAMPLE 3

Preparation of 6'-[[[(2-chloroethyl)nitrosoamino]carbonyl]amino]-6'-deoxysucrose (compound 1) (in the case where all the "R"s given in the general structural formula (I) denote a hydrogen atom, A$^1$ indicates a group of

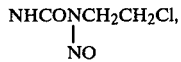

and A$^2$ represents a group of OR).

A 170 mg portion of 6'-[[[(2-chloroethyl)amino]carbonyl]amino]-6'-deoxysucrose was dissolved in 2 ml of formic acid. 50 mg of sodium nitrite was added to the solution in small portion under ice cooling and stirring. After 1 hour, the sodium ion was removed by the ion exchange resin Amberlite IR-120B (H+). The ion exchange resin was filtered off. The filtrate was concentrated in vacuo to give a yellow glass-like residue. The residue was purified by the silica gel column chromatography (solvent: a mixture of benzene and methanol bearing a ratio of 5:2). The purified matter was solidified with ethanol and ether to give 6'-[[[(2-chloroethyl)nitrosoamino]carbonyl]amino]-6'-deoxysucrose (compound 1) as powder.

Yield: 75 mg (40%).

Melting point: 60° C. (accompanied with foaming).

$[\alpha]_D^{23}$: +38.1° (C 2.1, water).

Infrared spectrum: 1495 cm$^{-1}$ (nitroso); 1530 cm$^{-1}$, 1725 cm$^{-1}$ (ureido).

| Elemental analysis of C$_{15}$H$_{26}$N$_3$O$_{12}$Cl (having a molecular weight of 475.839): | | |
|---|---|---|
| Calculated value: | C | 37.86 |
| (%) | H | 5.51 |
|  | N | 8.83 |
|  | Cl | 7.45 |
| Experimental value: | C | 37.81 |
| (%) | H | 5.69 |
|  | N | 8.55 |
|  | Cl | 7.44 |

EXAMPLE 4

Preparation of 6'-[[[(2-chloroethyl)nitrosoamino]carbonyl]amino]-6'-deoxysucrose (compound 1) (in the case where all the "R"s given in the general structural formula denote a hydrogen atom, A$^1$ indicates a group of

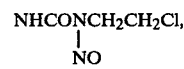

and A$^2$ represents a group of OR).

A 200 mg portion of 6'-[[[(2-chloroethyl)amino]carbonyl]amino]-6'-deoxysucrose was dissolved in 2 ml of acetone. Nitrogen trioxide gas was bubbled into the solution for 2 minutes under ice cooling and agitation. A residue obtained after concentrating the solution was purified by the silica gel column chromatography (solvent: a mixture of benzene and methanol bearing a ratio of 5:2). A glass-like purified mass was solidified with ethanol and ether to give 6'-[[[(2-chloroethyl)nitrosoamino]carbonyl]amino]-6'-deoxysucrose (compound 1) as powder.

Yield: 98 mg (46%).

Melting point: 62° C. (accompanied with foaming).

$[\alpha]_D^{22}$: +40.3° (C 1.8, water).

Infrared spectrum: 1495 cm$^{-1}$ (nitroso); 1530, 1725 cm$^{-1}$ (ureido).

| Elemental analysis of C$_{15}$H$_{26}$N$_3$O$_{12}$Cl (having a molecular weight of 475.839): | | |
|---|---|---|
| Calculated value: | C | 37.86 |
| (%) | H | 5.51 |
|  | N | 8.83 |
|  | Cl | 7.45 |
| Experimental value: | C | 37.80 |
| (%) | H | 5.55 |
|  | N | 8.53 |
|  | Cl | 7.39 |

EXAMPLE 5

Preparation of 6'-[[[(2-chloroethyl)nitrosoamino]carbonyl]amino]-6'-deoxysucrose heptaacetate (compound 2) (in the case where all the "R"s given in the general structural formula denote an acetyl group, A$^1$ represents a radical of

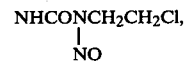

and A$^2$ indicates a group of OR).

A 51 mg portion of 6'-[[[(2-chloroethyl)nitrosoamino]carbonyl]amino]-6'-deoxysucrose (compound 1) was acetylated overnight at room temperature with 1 ml of pyridine and 1 ml of acetic anhydride. The reaction mixture was poured into ice cold water. Extraction was carried out with chloroform. The chloroform layer was washed with water and, dried over anhydrous sodium sulfate. The drying agent was filtered off, and the filrate was concentrated in vacuo. The resultant residue was purified by the silica gel column chromatography (solvent: a mixture of benzene and acetone bearing a ratio of 7:1) 6'-[[[(2-chloroethyl)nitrosoamino]carbony]amino]-6'-deoxysucrose heptaacetate (compound 2) as glass.

Yield: 47 mg (56.9%).

Melting point: 49° to 53° C.

$[\alpha]_D^{22}$: +55.3° (C 0.3, chloroform).

Infrared spectrum: 1500 cm$^{-1}$ (nitroso), 1540 cm$^{-1}$ (NH), 1750 cm$^{-1}$ (acetyl).

Elemental analysis of $C_{29}H_{40}N_3O_{19}Cl$ (having a molecular weight of 770.11):

| | | |
|---|---|---|
| Calculated value: | C | 45.23 |
| (%) | H | 5.24 |
| | N | 5.46 |
| | Cl | 4.60 |
| Experimental value: | C | 45.01 |
| (%) | H | 5.39 |
| | N | 5.58 |
| | Cl | 4.75 |

EXAMPLE 6

Preparation of 6-[[[(2-chloroethyl)nitrosoamino]carbonyl]amino]-6-deoxysucrose (compound 3) (in the case where all the "R"s given in the general structural formula denote a hydrogen atom, $A^1$ shows a group of OR, and $A^2$ represents a group of

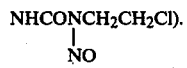

A 173 mg portion of 6-[[[(2-chloroethyl)amino]carbonyl]amino]-6-deoxysucrose was dissolved in 2 ml of formic acid. 45 mg of sodium nitrite was added into the solution in small portion under ice cooling and stirring. After 30 minutes, the sodium ion was removed by the ion exchange resin Amberlite IR-120B ($H^+$). The ion exchange resin was filtered off, and the filtrate was concentrated in vacuo to give a yellow glass-like residue. The residue was purified by the silica gel column chromatography (solvent: a mixture of benzene and methanol bearing a ratio of 5:2). The purified matter was solidified with ethanol and ether to give 6-[[[(2-chloroethyl)nitrosoamino]carbonyl]amino]-6-deoxysucrose (compound 3) as powder.

Yield: 76 mg (41%).
$[\alpha]_D^{18}$: +36.1° (C 0.36, methanol).
Melting point: 85° C. (accompanied with foaming).
Beilstein test: Positive (Cl).
Infrared spectrum: 1495 $cm^{-1}$ (NO), 1540 $cm^{-1}$ (ureido, NH), 1720 $cm^{-1}$ (ureido, C=O).
$^1H$ nuclear magnetic resonance spectrum (60 MHz, $D_2O$/DSS): δ 5.31 (d, 1H, $J_{1,2}$=3.21 Hz, H-1).

Elemental analysis of $C_{15}H_{26}N_3O_{12}Cl$ (having a molecular weight of 475.85):

| | | |
|---|---|---|
| Calculated value: | C | 37.86 |
| (%) | H | 5.51 |
| | N | 8.83 |
| | Cl | 7.45 |
| Experimental value: | C | 37.59 |
| (%) | H | 5.45 |
| | N | 8.61 |
| | Cl | 7.14 |

EXAMPLE 7

Preparation of 6-[[[(2-chloroethyl)nitrosoamino]carbonyl]amino]-6-deoxysucrose (compound 3) (in the case where all the "R"s given in the general structural formula denote a hydrogen atom, $A^1$ represents a group of OR, and $A^2$ shows a group of

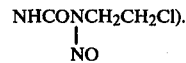

A 200 mg portion of 6-[[[(2-chloroethyl)amino]carbonyl]amino]-6-deoxysucrose was dissolved in 2 ml of acetone. Nitrogen trioxide gas was bubbled into the solution under ice cooling and stirring. A residue obtained by concentrating the reaction mixture was purified by the silica gel column chromatography (solvent: a mixture of benzens and methanol bearing a ratio of 5:2). The purified glass-like mass was solidified with ethanol and ether to give 6-[[[(2chloroethyl)nitrosoamino]carbonyl]amino]-6-deoxysucrose (compound 3) as a powder.

Yield: 98 mg (46%).
$[\alpha]_D^{20}$: +36.9° (C 0.22, methanol).
Infrared spectrum: 1495 $cm^{-1}$ (NO), 1540 $cm^{-1}$ (ureido, NH), 1720 $cm^{-1}$ (ureido, C=O).

Elemental analysis of $C_{15}H_{26}N_3O_{12}Cl$ (having a molecular weight of 475.85):

| | | |
|---|---|---|
| Calculated value: | C | 37.86 |
| (%) | H | 5.51 |
| | N | 8.83 |
| | Cl | 7.45 |
| Experimental value: | C | 37.55 |
| (%) | H | 5.59 |
| | N | 8.58 |
| | Cl | 7.55 |

EXAMPLE 8

Preparation of 6-[[[(2-chloroethyl)nitrosoamino]carbonyl]amino]-6-deoxysucrose (compound 3) (in the case where all the "R"s given in the general structural formula (I) denote a hydrogen atom, $A^1$ shows a group of OR, and $A^2$ represents a group of

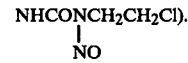

A 2.0 g portion of 6-amino-6-deoxysucrose was suspended in 150 ml of methanol, and 4 ml of triethylamine was added to the suspension at room temperature with stirring. Added to this suspension was a tetrahydrofuran solution of p-nitrophenyl-N-(2-chloroethyl)-N-nitrosocarbamate (4.4 g/100 ml). After 3 hours, the reaction mixture was concentrated in vacuo. The concentrated residue was purified by silica gel column chromatography (a soluvent: a mixture of benzene and methanol bearing a ratio of 5:2). The purified glass-like mass was solidified with ethanol and ether to give 6-[[[(2-chloroethyl)nitrosoamino]carbonyl]amino]-6-deoxysucrose (compound 3) as powder.

Yield: 1.52 g (55%).
$[\alpha]_D^{20}$: +35.3° (C 2.0, methanol).
Infrared spectrum: 1495 $cm^{-1}$ (NO), 1540 $cm^{-1}$ (ureido, NH), 1720 $cm^{-1}$ (ureido, C=O).

Elemental analysis of $C_{15}H_{26}N_3O_{12}Cl$ (having a molecular weight of 475.85):

| | | |
|---|---|---|
| Calculated value: | C | 37.86 |
| (%) | H | 5.51 |
| | N | 8.83 |
| | Cl | 7.45 |
| Experimental value: | C | 37.71 |

-continued

| Elemental analysis of $C_{15}H_{26}N_3O_{12}Cl$ (having a molecular weight of 475.85): | | |
|---|---|---|
| (%) | H | 5.38 |
| | N | 8.66 |
| | Cl | 7.29 |

EXAMPLE 9

Preparation of 6-[[[(2-chloroethyl)nitrosoamino]carbonyl]amino]-6-deoxysucroseheptaacetate (compound 4) (in the case where all the "R"s given the general structural formula (I) denote an acetyl group, $A^1$ represents a group of OR, and $A^2$ shows a group of

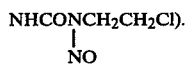

A 314 mg portion of 6-[[[(2-chloroethyl)nitrosoamino]carbonyl]amino]-6-deoxysucrose (compound 3) was treated with 3 ml of acetic anydride and 3 ml of pyridine. The mixture was allowed to stand overnight at room temperature. A residue obtained by concentrating the reaction mixture in vacuo was purified by silica gel column chromatography (a solvent: a mixture of benzene and acetone bearing a ratio of 9:1) to give 6-[[[(2-chloroethyl)nitrosoamino]carbonyl]amino]-6-deoxysucrose heptaacetate (compound 4) as glass.

Yield: 287 mg (57%),
$[\alpha]_D^{17}$: +48.4° (C 1.8, chloroform),
Melting point: 46° C.
Beilstein test: Positive (Cl).
Infrared spectrum: 1490 cm$^{-1}$ (NO), 1530 cm$^{-1}$ (ureido, NH), 1740 cm$^{-1}$ (acetyl, C=O).
$^1$H nuclear magnetic resonance spectrum (60 MHz, CDCl$_3$/TMS): δ 2.02 (s, 3H, OAc), 2.08 (s, 15H, OAc×5), 2.16 (S, 3H, OAc), 3.44 (t, 2H, J=6.01 Hz, CH$_2$CH$_2$Cl), 3.64 (t, 2H, J=6.01 Hz, CH$_2$CH$_2$Cl), 4.73 (dd, 1H, J$_{1,2}$=4.01 Hz, J$_{2,3}$=9.62 Hz, H-2), 4.91 (t, 1H, J$_{2,3}$=J$_{3,4}$=9,62 Hz, H-3), 5.61 (d, 1H, J$_{1,2}$=4.01 Hz, H-1).

| Elemental analysis of $C_{29}H_{40}N_3O_{19}Cl$ (having a molecular weight of 770.11): | | |
|---|---|---|
| Calculated value: | C | 45.23 |
| (%) | H | 5.24 |
| | N | 5.46 |
| | Cl | 4.60 |
| Experimental value: | C | 45.25 |
| (%) | H | 5.20 |
| | N | 5.33 |
| | Cl | 4.84 |

EXAMPLE 10

Preparation of 6-[[[(2-chloroethyl)nitrosoamino]carbonyl]amino]-6-deoxysucroseheptaacetate (compound 4) (in the case where all the "R"s given in the general structural formula (I) denote a acetyl group, $A^1$ shows a group of OR, and $A^2$ represents a group of

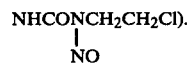

A 228 mg portion of 6-[[[(2-chloroethyl)amino]carbonyl]amino]-6-deoxysucrose heptaacetate was dissolved in 3 ml of formic acid, and 32 mg of sodium nitrite was added to the solution under ice cooling and agitation. After 1 hour, the reaction mixture was poured into ice cold water. Extraction was carried out with chloroform. The chloroform layer was washed with water, dried with anhydrous sodium sulfate. The dried solution was concentrated in vacuo to give a pale yellow glass-like residue. This residue was purified by the silica gel column chromatography (the ratio of the solvent to the mixture of benzene and acetone being the ratio of 9:1) to give 6-[[[(2-chloroethyl)nitrosoamino]-carbonyl]amino]-6-deoxysucrose heptaacetate (compound 4) as pale yellow glass.

Yield: 187 mg (79%).
$[\alpha]_D^{20}$: +49.9° (C 2.1, chloroform).
Melting point: 48° C.
Beilstein test: Positive (Cl).
Infrared spectrum: 1490 cm$^{-1}$ (NO), 1530 cm$^{-1}$ (ureido, NH), 1740 cm$^{-1}$ (acetyl, C=O).

| Elemental analysis of $C_{29}H_{40}N_3O_{19}Cl$ (having a molecular weight of 770.11): | | |
|---|---|---|
| Calculated value: | C | 45.23 |
| (%) | H | 5.24 |
| | N | 5.46 |
| | Cl | 4.60 |
| Experimental value: | C | 45.31 |
| | H | 5.21 |
| | N | 5.41 |
| | Cl | 4.72 |

What we claim is:
1. Nitrosourea derivatives of sucrose whose structure is expressed by the general formula:

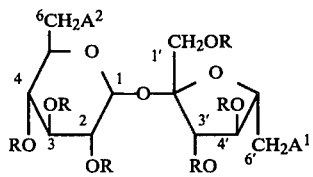

wherein one of $A^1$ and $A^2$ is

and the other is OR, and R is a hydrogen atom or an acyl group.

2. The nitrosourea derivatives according to claim 1, wherein $A^1$ is

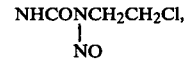

and $A^2$ is OR.

3. The nitrosourea derivatives according to claim 1, wherein $A^1$ is OR, and $A^2$ is

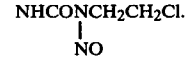

4. The nitrosourea derivatives according to claim 2 or 3, wherein all the "R"s are hydrogen atoms.

5. The nitrosourea derivative according to claim 2 or 3, wherein all the "R"s are acetyl groups.

* * * * *